United States Patent
Michaels et al.

(10) Patent No.: US 11,383,097 B2
(45) Date of Patent: Jul. 12, 2022

(54) LIGHT EMITTING HANDS FREE DEVICE

(71) Applicant: Lexington International, LLC, Boca Raton, FL (US)

(72) Inventors: David Michaels, Boca Raton, FL (US); Randy Veliky, Lighthouse Point, FL (US); James Smeriglio, Jupiter, FL (US); Alena Michaels, Boca Raton, FL (US)

(73) Assignee: Lexington International, LLC, Boca Raton, FL (US)

( * ) Notice: Subject to any disclaimer, the term of this patent is extended or adjusted under 35 U.S.C. 154(b) by 0 days.

(21) Appl. No.: 16/800,482

(22) Filed: Feb. 25, 2020

(65) Prior Publication Data

US 2020/0188688 A1 Jun. 18, 2020

Related U.S. Application Data

(63) Continuation of application No. 14/885,108, filed on Oct. 16, 2015, now abandoned.

(Continued)

(51) Int. Cl.
*A61N 5/06* (2006.01)
*A61M 37/00* (2006.01)
(Continued)

(52) U.S. Cl.
CPC .......... *A61N 5/0617* (2013.01); *A61M 37/00* (2013.01); *A61M 2037/0007* (2013.01);
(Continued)

(58) Field of Classification Search
CPC .......... A61B 18/20–18/28; A61M 2037/0007; A61M 37/00; A61N 2005/0626;
(Continued)

(56) References Cited

U.S. PATENT DOCUMENTS

2003/0004499 A1* 1/2003 McDaniel ............ A61B 18/203
606/3
2006/0287696 A1* 12/2006 Wright ................. A61N 5/0613
607/88
(Continued)

FOREIGN PATENT DOCUMENTS

WO  WO-2005115263 A1 * 12/2005 .......... A61N 5/0616
WO  2010067323 A1  6/2010
WO  2013084189 A2  6/2013

OTHER PUBLICATIONS

Korean Office Action dated May 22, 2019, for corresponding Application No. 2017-7013731; Filing Date: May 19, 2017 consisting of 16-pages.

(Continued)

*Primary Examiner* — Jonathan T Kuo
*Assistant Examiner* — Vynn V Huh
(74) *Attorney, Agent, or Firm* — Christopher & Weisberg, P.A.

(57) ABSTRACT

A light emitting device for a human having a scalp with hair, the device includes a flexible arcuate base configured to contour a portion of the scalp. The base has a width between 20 mm and 120 mm and includes an interior and an interior surface. At least one array of teeth is coupled to the interior surface, each tooth in the at least one array of teeth being pressed against the scalp when the base is contoured about the scalp. Each tooth is configured to part the hair when the at least one array of teeth is pressed against the scalp. An array of at least one of light emitting diodes and laser diodes coupled to the base proximate the at least one array of teeth.

15 Claims, 8 Drawing Sheets

Related U.S. Application Data (60) Provisional application No. 62/066,016, filed on Oct. 20, 2014.

(51) Int. Cl.
*A61N 5/067* (2006.01)
*A61H 7/00* (2006.01)
*A61H 11/00* (2006.01)

(52) U.S. Cl.
CPC ...... *A61N 5/067* (2021.08); *A61N 2005/0626* (2013.01); *A61N 2005/0643* (2013.01); *A61N 2005/0647* (2013.01); *A61N 2005/0652* (2013.01); *A61N 2005/0659* (2013.01); *A61N 2005/0662* (2013.01)

(58) Field of Classification Search
CPC .... A61N 2005/0643; A61N 2005/0647; A61N 2005/0652; A61N 2005/0659; A61N 2005/0662; A61N 5/067; A61N 5/0617
USPC ...................... 607/88–94; 606/2–19
See application file for complete search history.

(56) References Cited

U.S. PATENT DOCUMENTS

| | | |
|---|---|---|
| 2007/0150030 A1 | 6/2007 | Pearl et al. |
| 2010/0105977 A1 | 4/2010 | De Taboada et al. |
| 2010/0106077 A1* | 4/2010 | Rabin .................. A61N 5/0616 604/20 |
| 2011/0015707 A1* | 1/2011 | Tucker ................. A61N 5/0616 607/90 |
| 2011/0092863 A1* | 4/2011 | Kim ..................... A61N 5/0617 601/18 |
| 2014/0155962 A1 | 6/2014 | Deroberts |
| 2014/0296946 A1 | 10/2014 | Malek et al. |
| 2016/0128414 A1* | 5/2016 | Gotti ..................... A42B 3/085 2/421 |

OTHER PUBLICATIONS

English Translation of Taiwanese Notice of Allowance and Search Report dated Jul. 29, 2015, for Taiwanese Serial No. 104301118 filed Mar. 4, 2015 and Mandarin language Taiwanese Notice of Allowance and Search Report, consisting of 6 pages.

International Search Report and Written Opinion dated Jan. 20, 2016 for International Application No. PCT/US2015/055957, International Filing Date Oct. 16, 2015 consisting of 12 pages.

Written Opinion dated Sep. 27, 2016, for corresponding International Application No. PCT/US2015/055957; International Filing Date: Oct. 16, 2015 consisting of 6-pages.

Notification of Transmittal of The International Preliminary Report on Patentability dated Jan. 10, 2017, for corresponding International Application No. PCT/US2015/055957; International Filing Date: Oct. 16, 2015 consisting of 6-pages.

Chinese Office Action dated Oct. 17, 2018, for corresponding Application No. 201580068022.4; Filing Date: Jun. 9, 2017 consisting of 10-pages.

Korean Office Action dated Nov. 21, 2018, for corresponding Application No. 2017-7013731; Filing Date: May 19, 2017 consisting of 10-pages.

\* cited by examiner

LIGHT EMITTING HANDS FREE DEVICE

CROSS-REFERENCE TO RELATED APPLICATION

This application is a Continuation of U.S. patent application Ser. No. 14/885,108, filed on Oct. 16, 2015, entitled LIGHT EMITTING HANDS FREE DEVICE, which claims priority to U.S. Provisional Application Ser. No. 62/066,016, filed Oct. 20, 2014, entitled LIGHT EMITTING HANDS FREE DEVICE, the entirety of both which are incorporated herein by reference.

TECHNICAL FIELD

The present invention relates to light emitting hands free devices to stimulate hair growth.

BACKGROUND

Laser emitting combs and helmets have been devised to treat hair loss or otherwise stimulate new hair growth. Such devices, however, either provide for a single angle and/or position that therapeutic light can be emitted to the scalp, such as in a stationary helmet in which light may be obstructed by the user's existing hair, or require the user to remember which areas of the scalp were treated as the device is moved over the scalp, such as in a hair comb. In either case, there is a difficulty in ensuring that the entire scalp is treated with light with limited user involvement.

Helmet devices having lasers extending from the helmet toward the scalp have been devised to provide for hands-free light treatment of the scalp. However, such devices are not movable about the scalp, they simply press down onto the scalp or hair when the helmet is worn by the user. Thus, helmet devices provide no mechanism to part the user's existing hair such that the light reaches the scalp, but rather are limited to delivering light to wherever the helmet is positioned on the scalp, which may be obstructed by the user's hair.

SUMMARY

The present application provides a light emitting device for a human having a scalp with hair, the device includes a flexible arcuate base configured to contour a portion of the scalp. The base has a width between 20 mm and 120 mm and includes an interior and an interior surface. At least one array of teeth is coupled to the interior surface, each tooth in the at least one array of teeth being pressed against the scalp when the base is contoured about the scalp. Each tooth is configured to part the hair when the at least one array of teeth is pressed against the scalp. An array of at least one of light emitting diodes and laser diodes coupled to the base proximate the at least one array of teeth.

In another embodiment, a hair growth system for use with a human scalp having hair is included, the system includes a base configured to contour the scalp, the base including an interior and an interior surface and has a width of between 20 mm and 120 mm. At least two arrays of teeth are coupled to the interior surface, each tooth in the at least two arrays of teeth is pressed against the scalp when the base is contoured about the scalp. Each tooth is configured to part the hair when the at least two arrays of teeth are pressed against the scalp. An array of laser diodes is disposed within the interior between the at least two arrays of teeth. A control unit is in communication with and remote to the base, the control unit being configured to activate the array of laser diodes.

In yet another embodiment, the system includes a flexible arcuate base configured to contour the scalp, the base including an interior and an interior surface and having a width between 20 mm and 120 mm. At least two arrays of teeth coupled to the interior surface, each tooth in the at least two arrays of teeth being pressed against the scalp when the base is contoured about the scalp. Each tooth is configured to part the hair when the at least two arrays of teeth are pressed against the scalp. An array of laser diodes is disposed within the interior between the at least two arrays of teeth. The base is movable from a first position on the scalp to a second position of the scalp without the at least two arrays of teeth losing contact with the scalp. A resilient element is coupled to at least one of the at least two arrays of teeth, the resilient element configured to facilitate the movement of one of the at least two arrays of teeth from a first position away from the interior surface to a second position adjacent the interior surface. An image capture element is coupled to the base, the image capture element being configured to capture one or more images of the scalp when the base is contoured about the scalp. A control unit in communication with and remote to the base is included, the control unit being configured to activate the array of laser diodes; the control unit includes a processor configured to compare the captured one or more images of the scalp and determine the extent of follicle density and compile the one or more images of the scalp and determine whether substantially the entirety of the scalp has been exposed to light emitted from the array of laser diodes.

DETAILED DESCRIPTION

As used here, relational terms, such as "first" and "second," "over" and "under," "front and rear," and the like, may be used solely to distinguish one entity or element from another entity or element without necessarily requiring or implying any physical or logical relationship or order between such entities or elements.

Figures 1A, 1B, 1C:
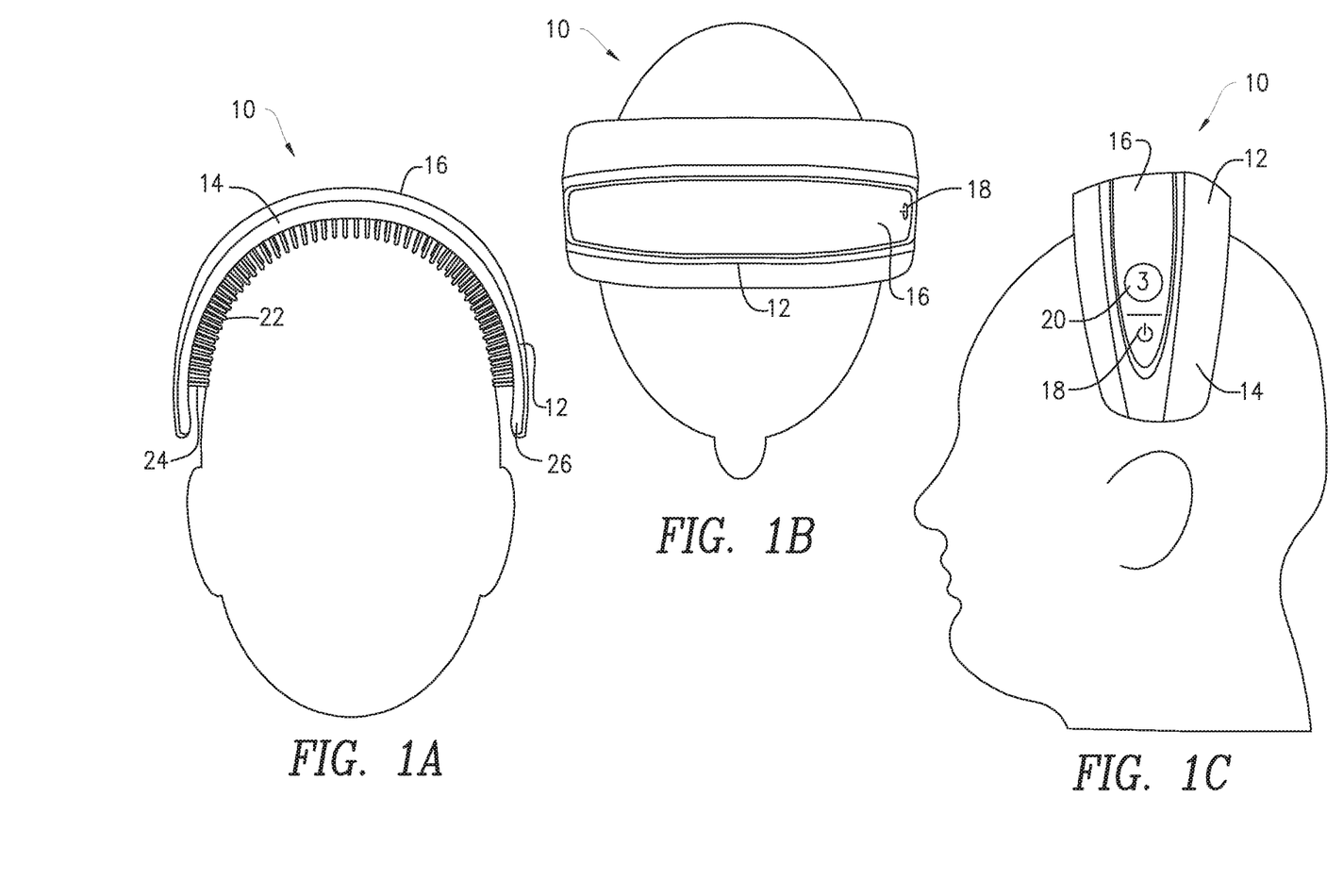
FIG. 1A is a front view of a light emitting hands free device constructed in accordance with the principles of the present application.
FIG. 1B is a top view of the light emitting device shown in FIG. 1A.
FIG. 1C is a side view of the light emitting device shown in FIG. 1A.

Referring now to the drawings in which like reference designators refer to like elements, there is shown in FIGS. 1A-1C an exemplary light emitting hands free device constructed in accordance with the principles of the present application and designated generally "10." The device 10 may be constructed of rigid materials such as polycarbonate and/or other elastic and resilient materials, such as thermoplastic polyurethane, or metals and metal alloys. In particular, the device 10 may include an elongate base 12 biased in a substantially arcuate or semi-circular configuration. In particular, the base 12 may include an exterior surface 14 composed of a resilient material shaped in substantially the same arc defined the top of human scalp extending between the user's two ears. The base 12 may extend from a position just above the user's left ear, across the scalp, and terminate at a position just above the user's right ear. In an exemplary configuration, the length of the base 12 is between approximately 175-240 mm and the width of the base is approximately 20-120 mm. The base 12 may define a sloped or curved surface along its width. For example, as shown in FIG. 1C, the base 12 may increase in height to a maximum height of approximately 140 mm as it extends from the front of the user's scalp to the back of the user's scalp and then may decrease in height as it extends toward the posterior of the scalp. It is contemplated that the base 12 may define any slope along its width or length to facilitate a proper contour of the base 12 about the user's scalp. For example, the base 12 may include an extension element (not shown) configured to provide an adjustment in the overall length of the base 12 to accommodate differently sized scalps. The extension element may, for example, be a telescoping member or resilient elastic member disposed within the interior of the base to increase the length of the base 12 as needed.

The base 12 may include a power panel 16 extending at least a portion of the length of the base 12, and in one configuration, substantially the entire length of the base 12. In the embodiments shown in FIGS. 1A-1C, the power panel 16 is positioned at approximately the center of the width of the base 12 and may be identified by a different color than that of the remainder of the base 12. The base 12 may define a recess (not shown) sized to receive the power panel 16. In one embodiment, the power panel 16 is releasably affixable to the base 12 within the recess such that it may be modular. In particular, the power panel 16 may readily snap into and out of the base 12 to connect the power panel 16. In other embodiments, the power panel 16 is permanently affixed to the base 12. The power panel 16 may include a rechargeable battery (not shown) such as a lithium ion battery, or a non-rechargeable battery, in communication with the various powered components of the device 10 discussed in more detail below, an on/off power switch 18, a timer 20, and a vibration adjustment actuator (not shown).

Figure 2A:
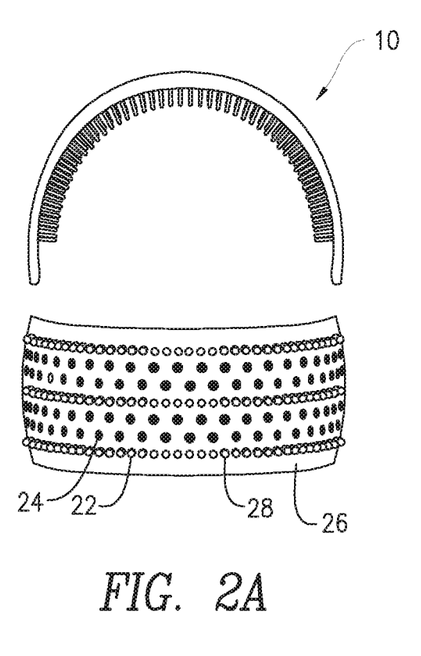
FIG. 2A is a side and inside-out surface view of an embodiment of the light emitting device shown in FIG. 1A.

Referring now to FIGS. 1A, and 2A-2C, the device 10 may include a plurality of teeth 22 and a plurality of diodes 24 disposed within an interior surface 26 of the base 12. The plurality of teeth 22 may be composed of a resilient or rigid material, for example polyurethane or polycarbonate, and a define a blunted edge as to be a traumatic to the scalps as the interior surface is positioned on and/or moved across the user's scalp. In an exemplary configuration, each of the plurality of teeth 22 taper inward in width as they extend away from the interior surface 26. The plurality of teeth 22 may be arranged in one or more arrays along the interior surface 26. For example, as shown in FIG. 2A, the plurality of teeth 22 are arranged in three substantially linear teeth arrays 28 along the interior surface 26. The teeth arrays 28 may be substantially parallel to one another and substantially equidistant from an adjacent teeth array 28. In the configuration shown in FIG. 2A, each tooth 22 in the teeth array 28 is spaced approximately 7 mm from an adjacent tooth 22 and span substantially the entire length of the interior surface 26 of the base 12. Each tooth 22 may be configured to part the user's hair as the base 12 is moved over the user's scalp, or to part hair while the base 12 is stationary over a particular part of the user's scalp. For example, the base 12 may be pivoted about the user's scalp, from front to back or from back to front, to a desired treatment region on the user's scalp while each tooth 22 maintains contact with the user's scalp and/or hair. The pivot point may be the ends of the base 12 proximate the ears. As the base 12 is moved over the user's scalp to a desired position, the user's hair may be pinned down or otherwise parted by the teeth 22 to provide for at least a substantially unobstructed pathway for the light emitted from the diodes 24 to treat the user's scalp.

Figure 3:
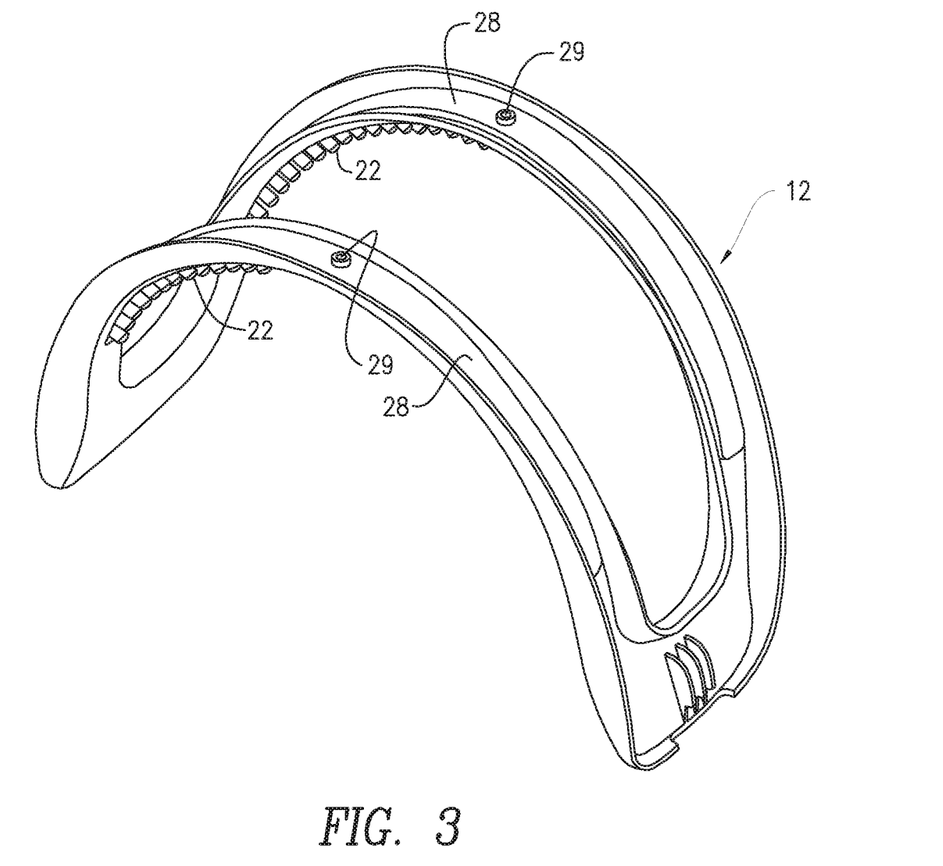
FIG. 3 is a side perspective component view of two arrays of teeth coupled to the base of the device shown in FIG. 1A.
Figure 4A:
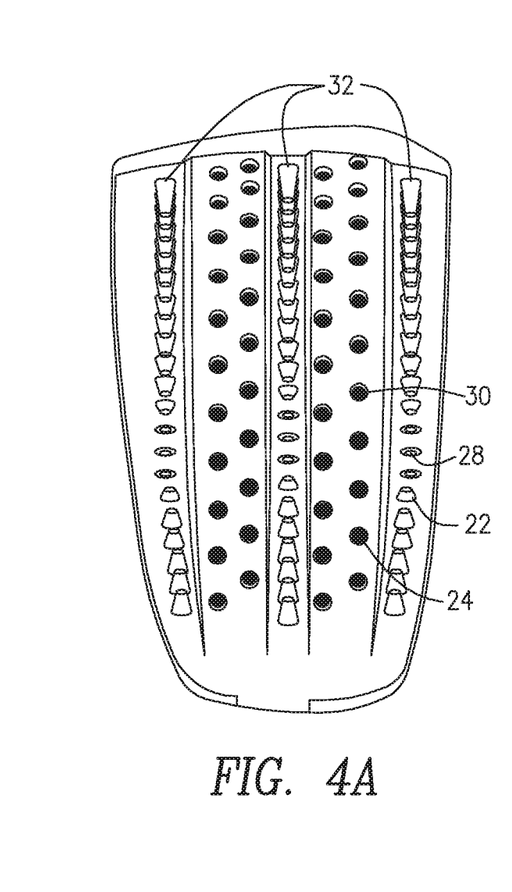
FIG. 4A is a side inside-out surface view of the embodiment of the light emitting device shown in FIG. 2A.
Figure 4B:
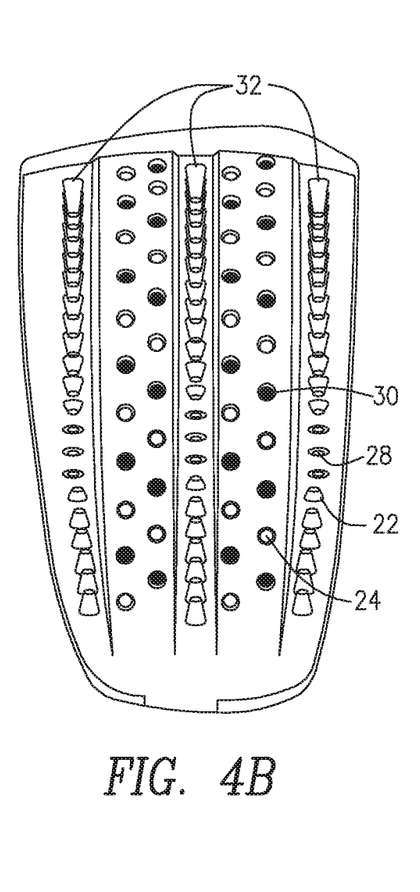
FIG. 4B is a side inside-out surface view of the embodiment of the light emitting device shown in FIG. 2B.
Figure 4C:
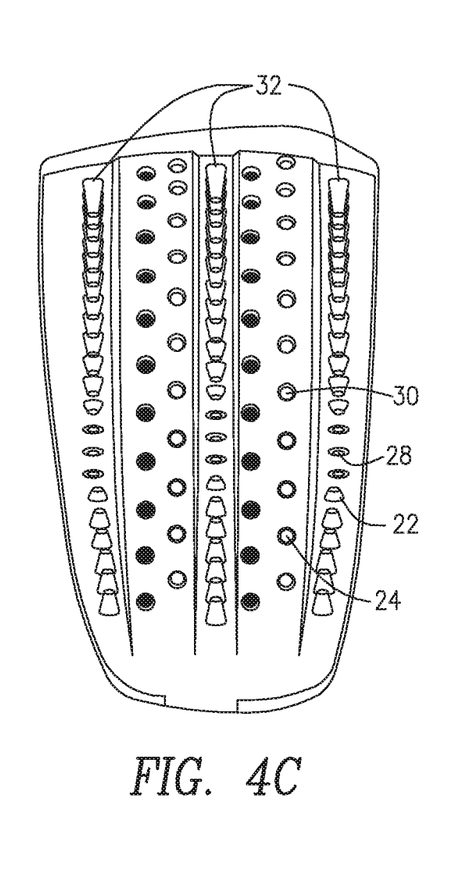
FIG. 4C is a side inside-out surface view of the embodiment of the light emitting device shown in FIG. 2C.
Figure 5A:
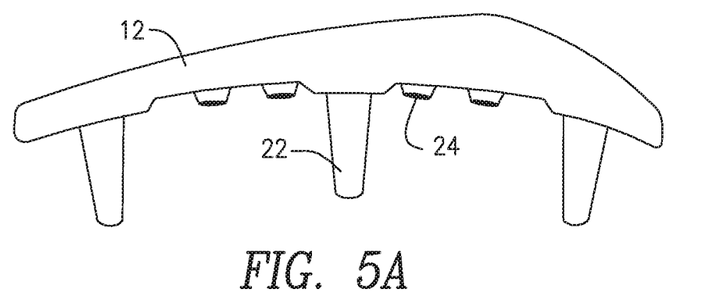
FIG. 5A is a side view of an embodiment of the light emitting device shown in FIG. 1A.
Figure 5B:
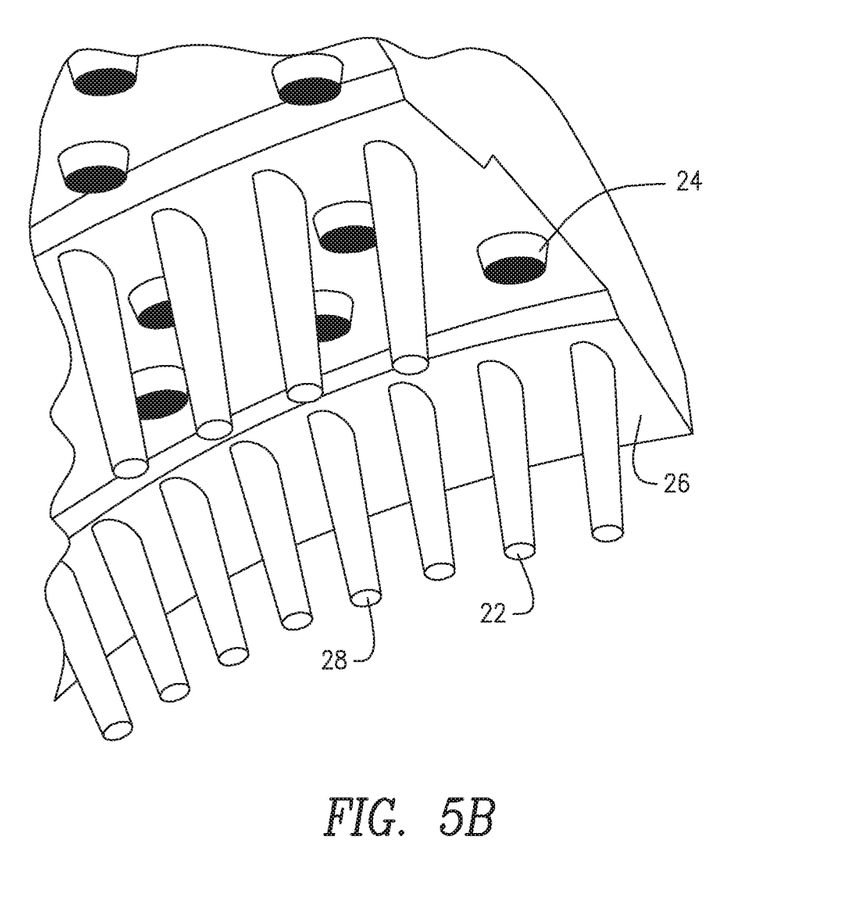
FIG. 5B is a side inside perspective view of the embodiment of the light emitting device shown in FIG. 1A.

Referring now to FIG. 3, one or more of the arrays 28 may further include a resilient element 29 positionable proximate the interior surface 26 and the array 28. The resilient element 29, which may be a spring or an elastic material, may facilitate the movement of the respective array 28 from a first position away from the interior surface 26 to a second position adjacent the interior surface 26. In particular, when the array 28 is coupled to the base 12, the resilient element 29 is disposed between the interior surface and the array 28, for example, as protrusion extending away from the array 28. When the user positions the base 12 onto the scalp, the resilient element 29 may be pressed against the interior surface 29 which allows the flexion of the respective array 28 where the force is applied, which may provide for comfort around the scalp and/or a better fit of the array 28 to the scalp.

Referring back now to FIGS. 2A-2C, each teeth array 28 may be spaced approximately 30 mm, for example, a range from 10 mm-50 mm, from an adjacent teeth array 28 to provide for a particular arrangement of diodes 24. For example, as shown in FIG. 2A, the diodes 24, may be arranged in diode arrays 30 similar to the teeth arrays 28. In the configuration shown in FIG. 2A, each diode 24, which may be a laser or light emitting diode, at any wavelength of light, or a combination of wavelengths of light, for example, multi-chromatic light, may be disposed between two teeth arrays 28 for a total of four diode arrays 30. One diode array 30 may emit laser light, while another may emit white light, or a light at a particular wavelength, for example, yellow, green, red, blue, infrared and in the wavelengths of approximate 610-690 nm, 400-500 nm, 800-900 nm, and 1000-1200 nm. For example, one diode array 30 may contain diodes 24 emitting light in the wavelength of 610-690 nm and another diode array 30 may contain diodes 24 emitting light in the wavelength of 1000-1200 nm. Alternatively, all the diodes 24 may emit light at a first wavelength and may be modular with diodes 24 or diode arrays 30 configured to emit light at a second wavelength different than the first wavelength.

In the configuration shown in FIG. 2A, each diode array 30 is substantially parallel to every other diode array 30 and may be longitudinally offset from an adjacent diode array 30 and/or every other diode array 30. For example, FIG. 2A shows a configuration of the device 10 with four diode arrays 30, each array having diodes 24 for a total of 82 diodes 24. The diodes 24 may be positioned such that each diode 24 has a different vertical and/or horizontal orientation than each and every other diode 24, such that each diode 24 targets a different area of the scalp. In other configurations, a single array of teeth 28 may be included along any horizontal positional, with diodes 24 disposed in arrays 30 on one or both sides of the array 28 such that the array 28 and the diodes are substantially parallel to each other, although any configuration and placement of the arrays 30 and one or more arrays 28 are contemplated.

Figure 2B:
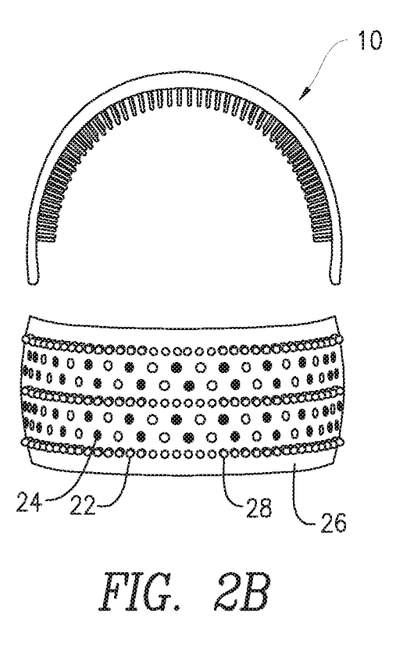
FIG. 2B is a side and inside-out surface view of an embodiment of the light emitting device shown in FIG. 1A.
Figure 2C:
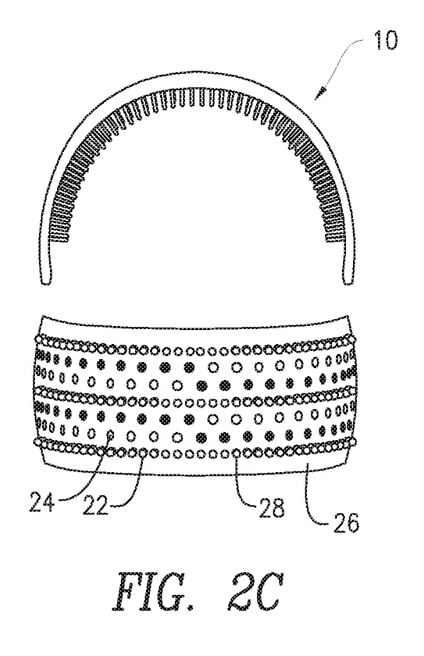
FIG. 2C is a side and inside-out surface view of an embodiment of the light emitting device shown in FIG. 1A.

In the configuration shown in FIG. 2B, two diode arrays 30 may be disposed between two teeth arrays 28 for a total of four diode arrays 30, however, half the number of diodes 24 are included in each diode array 30. In particular, in each diode array 30, 11 diodes are included as opposed to 22 diodes per diode array 30 as shown in FIG. 2A. To achieve the configuration shown in FIG. 2B, the power panel 16 shown in FIG. 2A may be substituted for the power panel 16 shown in FIG. 2B, or alternatively, the diodes 24 may be deactivated by the user for a particular treatment optionally programmed into the power panel 16 such that every other diode 24 is deactivated. Alternatively, the deactivated diodes 24 may be replaced by nubs or other non-electric material to space the activated diodes 24 from one another. Similar to FIG. 2B, the configuration shown in FIG. 2C includes four diode arrays 30 of 11 diodes with half of the diodes 24 in each diode array 30 being deactivated. In particular, each diode array 30 includes 11 consecutive diodes 24 that are activated followed by eleven consecutive deactivated diodes 24 or other non-electric material. As shown in FIG. 2C, each diode array 30 includes the opposite configuration of activated diodes 24 compared to an adjacent diode array 30.

Now referring to FIGS. 4A-4C, 5A-B, and FIG. 6, the teeth arrays 28 may be disposed in channels 32 defined by the base 12. In particular, each tooth 22 may extend away from the interior surface 26 from one channel 32 such that each teeth array 28 defines an arcuate configuration. Each diode 24 is positioned between at least two teeth 22 to facilitate the light emitted from each diode 24 being substantially unobstructed when a beam of laser light or non-laser light is emitted to the scalp. Alternatively, no channels 32 may be included and the proximal end of each tooth 22 may be substantially planar to a corresponding diode 24. Alternatively, each diode 24 and each diode array 30 may be recessed with respect to the arrays of teeth 28. For example, each diode 24 may be enclosed within an interior of the base 12, for example, by a transparent cover, that allows light to be emitted from each diode 24 while maintaining a smooth interior surface 26. In such a configuration, the base may be watertight or substantially watertight such that water does not enter the interior to damage the diodes 24.

Figure 7:
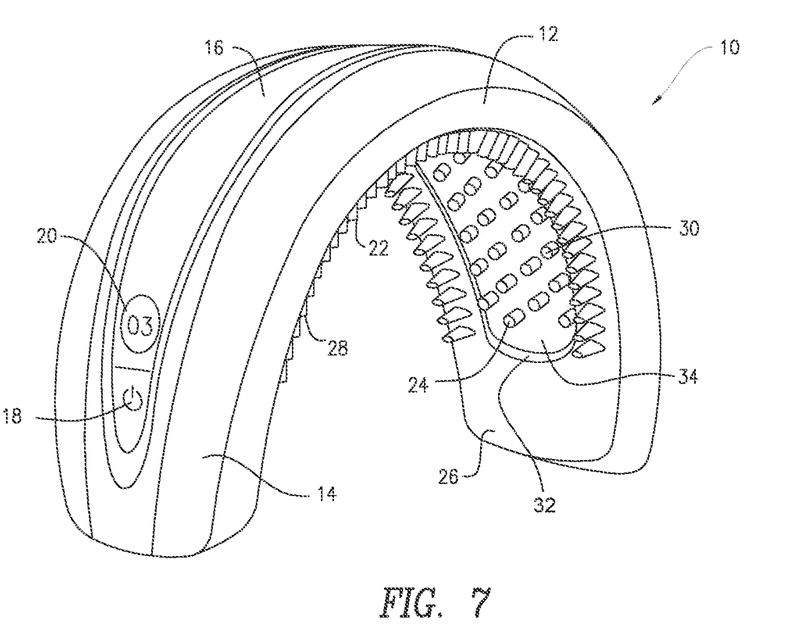
FIG. 7 is a side perspective view of another embodiment of the light emitting device constructed in accordance with the principles of the present application being disposed around a user's head and in communication with a portable electronic device.
Figure 8:
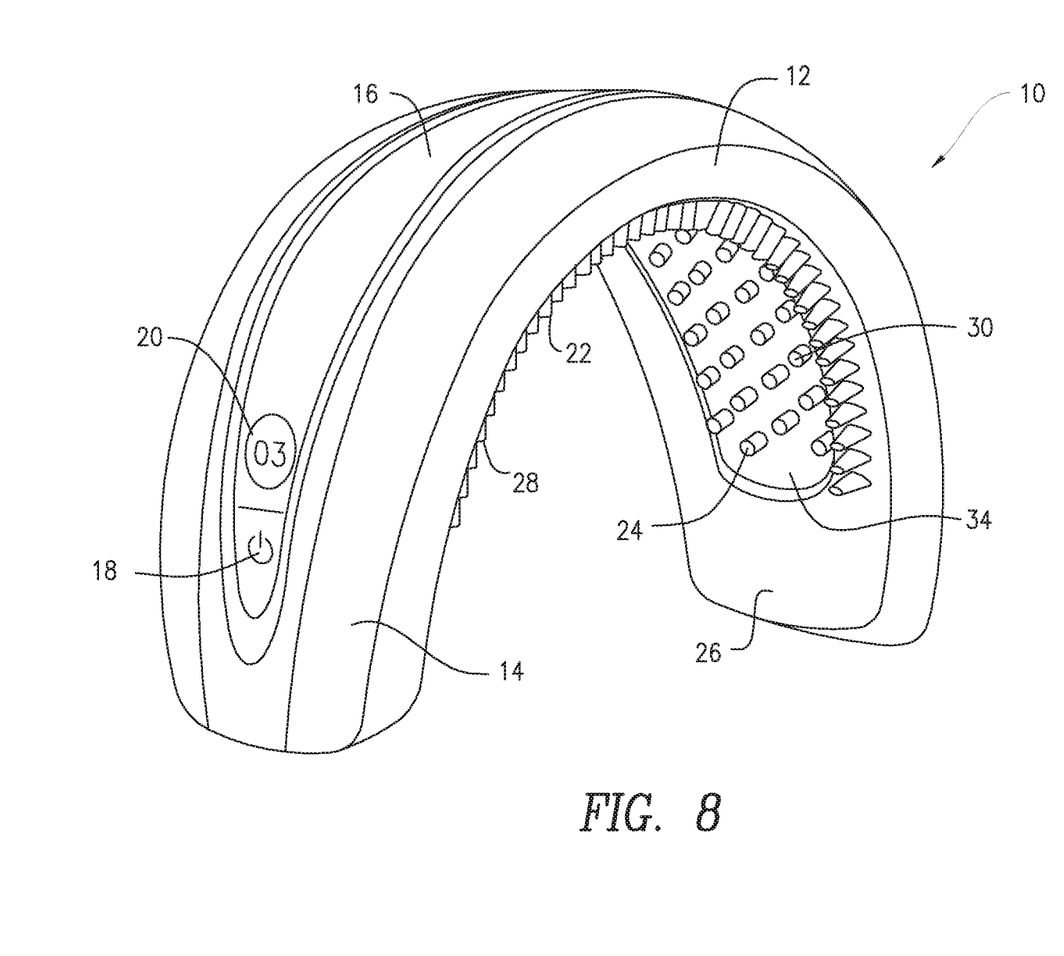
FIG. 8 is side perspective of the embodiment shown in FIG. 7 with one array of teeth.

In the configuration shown in FIG. 7, two arrays of teeth 28 are disposed on the interior surface 26. In FIG. 8, one array of teeth 28 is included adjacent the diode arrays 30 and may be on either side of the diode arrays 30. In either configuration, each array of teeth 28 is configured to part the user's hair as the base 12 is moved and/or pivoted about the scalp. In the configuration shown in FIG. 7, the arrays of teeth 28 are disposed toward the edges of the interior surface 26 creating a single channel 32 substantially spanning the width between the two arrays of teeth 28 and substantially spanning the length of the base 12. Removeably insertable within the channel 32 may be modular band 34 lockingly engageable within the channel 32. The band 34 may snap-fit within the channel 32 and be in electrical communication with the power panel 16 when inserted within the channel 32. Affixed to the band 34 are the plurality of diodes 24 and arrays 30, which may be arranged in any pattern and any number of arrays 30. For example, four arrays 30 are included in the embodiment in FIG. 7. It is further contemplated that other bands 34 may be snap-fit within the channel 32 to provide for a particular configuration of diodes 24, which may each emit light in a particular wavelength range of light as discussed above. In such a configuration, the modular band 34 may form a water tight seal within the interior surface 26.

Figure 6:
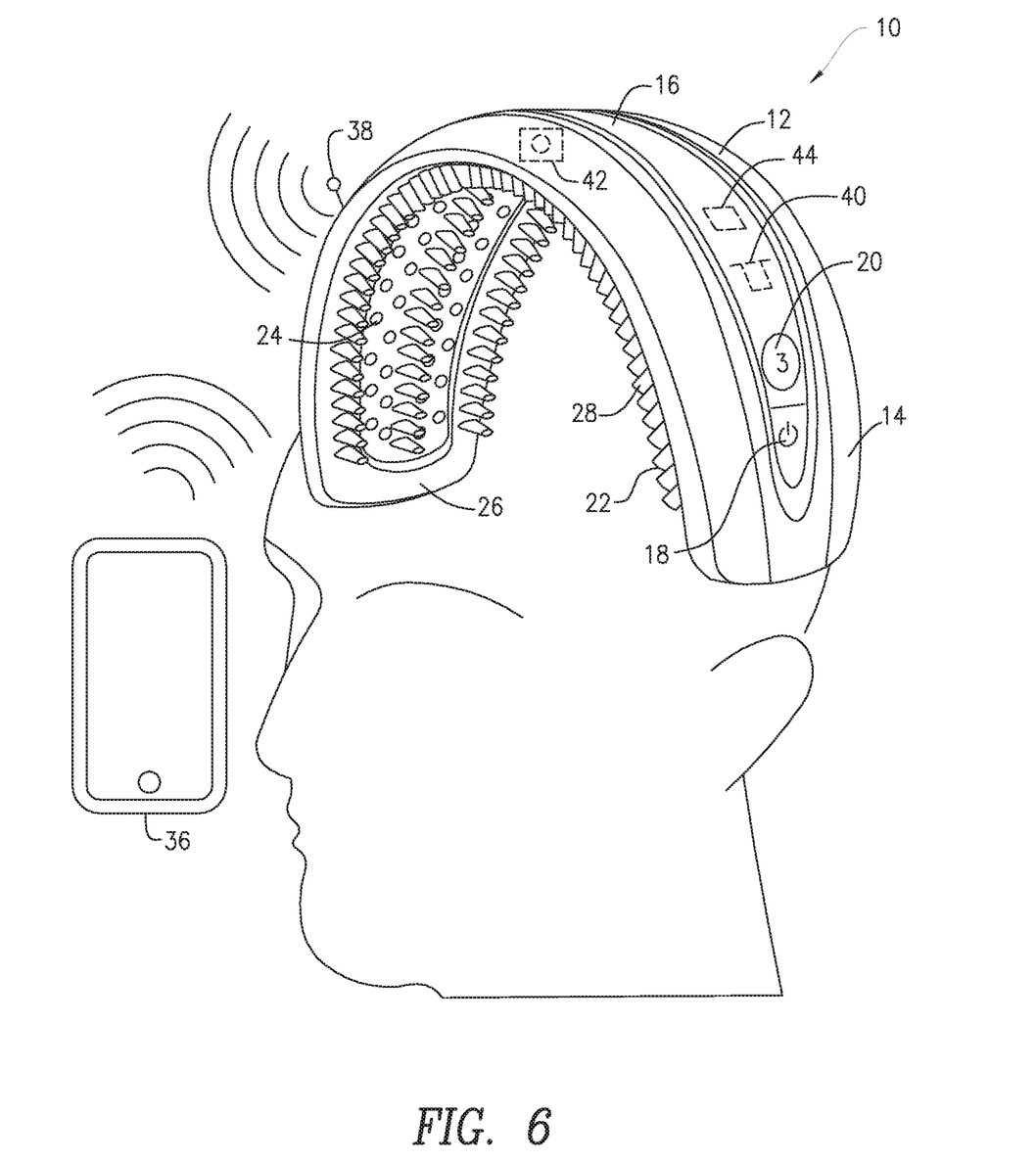
FIG. 6 is a side perspective view of another embodiment of a light emitting device constructed in accordance with the principles of the present application.

In an exemplary method of use of any of the above-described embodiments, the user positions the interior surface 26 over a front portion of the scalp and activates the device 10 with the on/off switch 18, or remotely, as discussed in more detail below, which activates the timer 20 to count down from a predetermined treatment time. For example, the diode arrays 30 may be activated for 3 minutes, or any duration, and then turn off. During those three minutes, the teeth arrays 28 may vibrate to aid in the part of the hair and/or provide gentle massage to the scalp. In a particular configuration, neither the teeth 22 nor the user's hair obstruct the pathway of light emitting from the diodes 24. After the predetermined about of time, an alert may sound to indicate to the user that the predetermined time period has concluded. The user may then pivot or otherwise move the device 10 to a different orientation of the scalp, for example the front of the scalp, the middle of the scalp (as shown in FIG. 6) or the rear of the scalp and continue treatment for an additional predetermined amount of time without removing the device 10 from the scalp and/or losing contact with the teeth 22 from the scalp or hair such that the hair may be parted by the teeth 22 to create an unobstructed, or substantially unobstructed, light path from the diodes 24 to the scalp. In particular, the user may shift the base 12 from a first position proximate the center of the scalp to a second position proximate the front or rear of the scalp without disengaging the base 12 from being pressed against the scalp.

Continuing to refer to FIG. 6, the device 10, and in particular the panel 16, may be in communication with a control unit 36 configured to activate and control the device 10 and optionally monitor treatments associated with the device 10. The control unit 36 may be a watch with a wireless transmitter, for example, the Apple Watch™, or a Smartphone, tablet computer, or a computer running application software configured to communicate with the device 10. In particular, the device 10 may include a wireless transmitter/receiver 38 in communication with a processor 40 in the base 12 configured to processes the various commands received from the control unit 36. For example, the Smartphone, such as an iPhone™, may have an application configured to be operable by the user to turn on/off the device 10, activate the diodes 24, turn on/off the timer of the device, turn on/off the teeth arrays 28, activate an image capture element 42 coupled to the base 12, and dispense a fluid from the base 12. In a particular configuration, the image capture element 42, which may be a camera coupled to the interior surface 26, may be configured to image sections of the scalp, when the base 12 is disposed or otherwise contoured about the user's scalp. The image capture element 42 may be substantially planar with the interior surface 26 as to not protrude a distance away from the interior surface 26. Alternatively, the image capture element 42 may protrude a distance away from the interior surface and may be positioned on a gimbal or structure configured to allow multiple axes of movement of the image capture element 42. Although not shown, the base 12 may also be foldable. For example, the base 12 may include a hinge proximate one or both ends of the base proximate the ears of a user when the device 10 is placed on a user's scalp. The hinge may allow for a portion of the base to fold to an angle of at least 90 degrees to allow the device 10 to be laid flat and stand on its own on a surface.

The software application in the control unit 36 may be in communication with the image capture element 42 and may activate the image capture element 42 either automatically when the device 10 is activated or manually by the user. In an exemplary configuration, when the user uses the device 10, the image capture element 42 captures an image of a section of the scalp. The image of the scalp is then analyzed to determine an average density of hair follicles and/or extent of hair growth in that imaged section. Each time the user uses the device 10 and treats the scalp with laser and/or light diodes 26, the image capture element 42 captures an image of the treated section and compares it overtime. The change in follicle density is calculated overtime and displayed on the display of the control unit such that the user can track the progress of treatments. For example, images captured by the image capture element 42 may be compiled to determine if the entire scalp and/or the desired portion of the scalp has been treated with light therapy and the extent of hair growth/follicle density on the scalp as a whole or a target portion of the scalp. The application may further be configured to calculate the change in follicle density and/or extent of hair growth based on a number of factors. For example, the application may include an algorithm that correlates the extent of hair growth and/or follicle density based on at least one of a frequency of use of the base 12, a duration of time per each use of the base 12, and the one or more captured images of the scalp. The user may further be able to track his/her progress over time to identify areas of the scalp that may require longer treatment times or a different light intensity. The base 12 may further include a reservoir 46 configured to store a hair growth stimulating fluid. The control unit 36 may be in communication with the reservoir 46 and configured to dispense fluid from the reservoir 46 either out through an aperture in the base 12 in fluid communication with the reservoir 46, or alternatively out through one or more teeth 22, which may have apertures at their respective distal ends in communication with the reservoir 46.

Moreover, the user data may be stored in the application and a user profile generated based on the data, such that multiple users may use the device 10 and a user specific treatment program may be tailored for the individual needs of the user. For example, the algorithm may determine for a particular user that the treatment time may need to be increased proximate the top of the scalp, as opposed to the front or back, and initiate a treatment program targeted toward hair growth in that particular region. To further determine that that the device 10 is moved or otherwise pivoted at a desired velocity about the scalp, the base 12 may include an accelerometer 44 in communication with the processor 40 to record the speed and/or acceleration at which the device is moving. If the device is moved above or below a predetermined speed, the device may vibrate or otherwise alert the user through a sound from the device or alert from the Smartphone 36 to increase or decrease the speed of parting the user's hair with the teeth array 28.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A light emitting device for a human having a scalp with hair, comprising:
    a flexible arcuate base configured to contour a portion of the scalp and defining a curvature, the base having a width between 20 mm and 120 mm, the base including an interior and an interior surface;
    two curvilinear arrays of teeth coupled to the interior surface and disposed along opposite sides of the base, each tooth in the two arrays of teeth being pressable against the scalp when the base is contoured about the scalp, each tooth being configured to part the hair when the base is stationary over the scalp and the two arrays of teeth are pressed against the scalp, each of the two arrays of teeth defining a curvature the same as the curvature of the flexible arcuate base;
    four curvilinear and parallel arrays of laser diodes coupled to the base and disposed between the two arrays of teeth, each one of the laser diodes being recessed and spaced apart from each tooth in the two arrays of teeth and being longitudinally offset from an adjacent laser diode in an adjacent one of the four curvilinear and parallel arrays of laser diodes, the four curvilinear and parallel arrays of laser diodes defining a curvature the same as the curvature of the flexible arcuate base, each one of the laser diodes being set apart from the two arrays of teeth;
    a channel defined by the interior of the base, the channel being entirely disposed between the two curvilinear arrays of teeth; and
    a modular band releasably affixed within the channel and forming a water-tight seal with the interior surface of the base.

2. The device of claim 1, wherein the four arrays of laser diodes are coupled to the modular band.

3. The device of claim 2, wherein the channel defines a curvature the same curvature as that of the base.

4. The device of claim 1, wherein the four arrays of laser diodes include 82 diodes.

5. The device of claim 1, wherein the two arrays of teeth are configured to part the hair of the scalp when the base is moved from a first position on the scalp to a second position of the scalp.

6. The device of claim 1, wherein each array of teeth includes more than one tooth that is separate and distinct from each one of the laser diodes.

7. The device of claim 6, wherein each tooth is made of a rigid material and includes a proximal end proximate to the interior surface of the base and an opposite distal end defining a blunted edge shaped to be atraumatic to the scalp.

8. The device of claim 7, wherein the blunted edge is formed as a unitary structure with each tooth of the two arrays of teeth.

9. The device of claim 8, wherein each tooth in the two arrays of teeth is spaced apart from an adjacent tooth at a distance of approximately 7 mm.

10. A light emitting device for a human having a scalp with hair, comprising:
   a flexible arcuate base configured to contour a portion of the scalp and defining a curvature, the base having a width between 20 mm and 120 mm, the base including an interior and an interior surface;
   two curvilinear arrays of teeth coupled to the interior surface and disposed along opposite sides of the base, each tooth in the two arrays of teeth being pressable against the scalp when the base is contoured about the scalp, each tooth being configured to part the hair when the base is stationary over the scalp and the two arrays of teeth are pressed against the scalp, each of the two arrays of teeth defining a curvature the same as the curvature of the flexible arcuate base;
   two curvilinear and parallel arrays of laser diodes coupled to the base and disposed between the two arrays of teeth, each one of the laser diodes being recessed and spaced apart from each tooth in the two arrays of teeth and being longitudinally offset from an adjacent laser diode in an adjacent array of the two curvilinear arrays of laser diodes, the two curvilinear arrays of laser diodes defining a curvature the same as the curvature of the flexible arcuate base;
   each tooth in the two arrays of teeth being made of a rigid material and including a proximal end proximate to the interior surface of the base and an opposite distal end defining a blunted edge shaped to be atraumatic to the scalp, the blunted edge being formed as a unitary structure with each tooth of the two arrays of teeth;
   a channel defined by the interior of the base, the channel being entirely disposed between the two curvilinear arrays of teeth; and
   a modular band releasably affixed within the channel and forming a water-tight seal with the interior surface of the base.

11. The device of claim 10, wherein the two arrays of teeth are configured to part the hair of the scalp when the base is moved from a first position on the scalp to a second position of the scalp.

12. The device of claim 10, wherein the two arrays of laser diodes are coupled to the modular band.

13. The device of claim 12, wherein the channel defines a curvature the same curvature as that of the base.

14. A light emitting device for a human having a scalp with hair, comprising:
   a flexible arcuate base configured to contour a portion of the scalp and defining a curvature, the base having a width between 20 mm and 120 mm, the base including an interior and an interior surface;
   two curvilinear arrays of teeth coupled to the interior surface and disposed along opposite sides of the base, each tooth in the two arrays of teeth being pressable against the scalp when the base is contoured about the scalp, each tooth tapering inwards in width as each tooth extends away from the interior surface of the base and being configured to part the hair when the base is stationary over the scalp and the two arrays of teeth are pressed against the scalp, each of the two arrays of teeth defining a curvature the same as the curvature of the flexible arcuate base;
   four curvilinear and parallel arrays of laser diodes coupled to the base and disposed between the two arrays of teeth, each one of the laser diodes being recessed and spaced apart from each tooth in the two arrays of teeth and being longitudinally offset from an adjacent laser diode in an adjacent one of the four curvilinear arrays of laser diodes, the four curvilinear arrays of laser diodes defining a curvature the same as the curvature of the flexible arcuate base;
   a channel defined by the interior of the base, the channel being entirely disposed between the two curvilinear arrays of teeth; and
   a modular band releasably affixed within the channel and forming a water-tight seal with the interior surface of the base.

15. The device of claim 14, further including:
   a resilient element coupled to at least one array of teeth from the two arrays of teeth at a location between the at least one array of teeth and the interior surface of the base, the resilient element being one of a spring and an elastic material configured to facilitate movement of the at least one array of teeth from a first position distal to the interior surface of the base to a second position adjacent and proximate to the interior surface of the base.

* * * * *